US00PP12518P2

(12) United States Plant Patent

Slaughter et al.

(10) Patent No.: US PP12,518 P2

(45) Date of Patent: Apr. 2, 2002

(54) NECTARINE TREE NAMED 'BURNECTONE'

(75) Inventors: John K. Slaughter, Clovis; Timothy J. Gerdts, Kingsburg, both of CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 09/461,665

(22) Filed: Dec. 14, 1999

(51) Int. Cl.[7] ..... A01H 5/00

(52) U.S. Cl. ..... Plt./192

(58) Field of Search ..... Plt./192

*Primary Examiner*—Bruce R. Campell
*Assistant Examiner*—Susan B. McCormick
(74) *Attorney, Agent, or Firm*—Wells, St. John, Roberts, Gregory & Matkin, P.S.

(57) ABSTRACT

A new and distinctive variety of nectarine tree denominated varietally as 'Burnectone', and which is characterized as to novelty by a date of maturity for commercial harvesting and shipment of approximately May 25 to June 5, under the ecological conditions prevailing in the San Joaquin Valley of Central California.

2 Drawing Sheets

BACKGROUND OF THE NEW VARIETY

The present invention relates to a new, novel and distinct variety of nectarine (*Prunus persica*) tree, which has been denominated varietally as 'Burnectone'. The 'Burnectone' Nectarine Tree produces an exceptionally high quality, freestone nectarine which is ripe for harvesting and shipment in the early season. Another unique aspect of the 'Burnectone' is that it yields a firm nectarine having a very high eating quality.

ORIGIN

The present variety of nectarine tree was derived from an ongoing program of fruit and nut tree breeding. The purpose of this program is to improve the commercial quality of deciduous fruit and nut varieties and rootstocks by creating and releasing selections of prunus, malus and regia species. To this end, we make both controlled and hybrid crosses each year in order to produce seedling populations from which improved progenies are evaluated and selected.

The nectarine seedling 'Burnectone' was originated by us in 1993, and chosen from among a population of seedlings which resulted from an open pollinated seedling of the 'May Diamond' Nectarine Tree (U.S. Plant Pat. No. 5,454). Resulting seed was planted in the spring of 1994. The resulting seed from this cross was planted in the spring of 1995. The new variety was selected from among the seedlings then growing in experimental orchards near the city of Fowler, Calif., County of Fresno, in the central San Joaquin Valley. The 'Burnectone' Nectarine Tree was subsequently marked and noted as having exceptional characteristics. This new variety has been repeatedly evaluated during fruiting seasons from 1995–1999. After the 1995 season, the Nectarine Tree 'Burnectone' was selected for advanced evaluation and repropagation. Characteristics as described hereinafter are derived from observations of the new variety as grown on 'Nemared' rootstocks (unpatented) as well as the original seedling grown on its own root.

ASEXUAL REPRODUCTION

Scionwood from the original seedling of the Nectarine Tree, 'Burnectone' was collected and grafted in the evaluation plot of the experimental orchards previously described, onto two different and existing 'Nemared' rootstocks (unpatented) in February of 1996. Fruit from the resulting propagation has been repeatedly evaluated for the 1997, 1998 and 1999 fruiting seasons. This evaluation has demonstrated that the repropagated trees are true to the characteristics of the original seedling in all observable aspects.

SUMMARY OF THE NEW VARIETY

The 'Burnectone' Nectarine Tree is characterized as to novelty by producing fruit which ripen in the early season. Further, the fruit of this new variety is considered of very high quality, is firm, and has an attractive exterior coloration. In this regard, the present variety of nectarine tree bears freestone fruit which are ripe for commercial harvesting and shipment approximately May 25 to June 5. These harvesting dates are before the harvest of the commercial freestone varity 'May Diamond' Nectarine Tree (U.S. Plant Pat. No. 5,454). Further, the present variety distinguishes itself from the 'May Diamond' Nectarine Tree by its brighter exterior coloration, flavor, and lower flesh acidity. The present variety also exhibits a lower frequency of split pits than does the fruit produced by the 'May Diamond' Nectarine Tree.

BRIEF DESCRIPTION OF THE DRAWING

The accompanying drawing are two color photographs, one of a characteristic twig bearing typical leaves; several leaves showing both the dorsal and ventral coloration thereof; and a second photograph displaying several mature fruit showing their external coloration sufficiently matured for harvesting and shipment. Additionally, one fruit of the subject variety is dissected in the equatorial or cheek plane to illustrate the flesh and stone characteristics.

DETAILED DESCRIPTION

Referring more specifically to the pomological details of this new and distinct variety of nectarine tree, the following has been observed under the ecological conditions prevailing at the orchards located near the town of Fowler, county of Fresno, state of California. All major color code designations are by reference to The R.H.S. Colour Chart (1995

Third Edition) provided by The Royal Horticultural Society of Great Britain.

Tree:

*Size.*—Generally — Average to above average as compared to other common nectarine cultivars.

*Productivity.*—Productivity with respect to pounds per acre is not available and is quite dependent on cultural practices. Consequently this characteristic is not distinctive of the variety.

*Figure.*—The original seedling was trained in a central leader configuration with a moderate spread in the crown of the tree. The tree is considered upright to upright spreading in form.

*Height.*—The original seedling had a height dimension of 3.1 m at the end of the 1999 growing season.

*Width.*—The original seedling tree had a 1.88 m width at the end of the 1999 growing season.

*Current season growth.*—The current season growth for the new variety was approximately 0.70–0.82 m.

*Regularity of bearing.*—Regular, and considered hardy under typical Central San Joaquin Valley conditions.

Trunk:

*Diameter.*—Approximately 81 mm in diameter when measured at a distance of approximately 15.24 cm above the soil level, at the end of the 1999 growing season.

*Bark texture.*—Considered moderately rough with numerous folds of papery scarf skin being present.

*Lenticels.*—Numerous flat, oval lenticels are present. The lenticels range in size from approximately 3.0 to 7.0 millimeters in width and from approximately 1 to 2 millimeters in height.

*Lenticels.*—Color — RHS Greyed Orange Group 173D.

*Bark coloration.*—Variable, but it is generally considered to be a grey-brown (RHS Greyed-Brown Group 174 A).

Branches:

*Size.*—Considered medium for the variety.

*Diameter.*—The branches have a diameter of approximately 31 mm when measured during the 3$^{rd}$ year after grafting.

*Surface texture.*—Average, and appearing furrowed on wood which is several years old.

*Crotch angles.*—Variable between about 42° to 47° from the horizontal axis for scaffold limbs. This is not distinctive of this variety however.

*Current season shoots.*—Surface Texture — Substantially glabrous.

*Internode length.*—Approximately 2.3 to 2.5 cm.

*Color of mature branches.*—Medium brown, (RHS Greyed Orange Group 175 C to 177 B).

*Current season shoots.*—Color — Light green, (RHS Yellow Green Group 144 C), with some reddish-brown coloration appearing on exposed exterior shoots (RHS Greyed Red Group 181 B). The color of the new shoot tips is considered a bright and shiny green (RHS Green Group 143 B).

Leaves:

*Size.*—Considered average for the species. Leaf measurements have been taken from vigorous upright current season growth at approximately midshoot.

*Leaf length.*—Approximately 162 to 165 millimeters.

*Leaf width.*—Approximately 48 to 52 millimeters.

*Leaf thickness.*—Approximately 1 to 2 millimeters.

*Leaf base shape.*—Slightly oblique.

*Leaf form.*—Lanceolate.

*Leaf tip form.*—Acuminate.

*Leaf color.*—Dark green (RHS Yellow Green Group 146 D).

*Leaf texture.*—Glabrous.

*Lower surface.*—Light green, (RHS Yellow Green Group 154 D).

*Venation.*—Pinnate.

*Mid-Vein.*—Color — Light yellow green, (RHS Yellow Green Group 153 B).

*Leaf margins.*—Form — Considerate crenate, occasionally doubly crenate. Uniformity — Considered generally uniform.

*Leaf petioles.*—Size — Considered medium. Length — Approximately 9 to 12 millimeters. Diameter — Approximately 1.5 to 2 millimeters. Color — Pale green, (RHS Yellow Green Group 150 C).

*Leaf glands.*—Size — Approximately one to two millimeters in height and two to three millimeters in width. Numbers — Generally 2–3 per side. Occasionally one per side. Type — Tight, small and globose. Color — Greenish brown, (RHS Grey Brown 199 C).

*Leaf stipules.*—Size — Approximately 8.0–11.0 mm in length; 1.0 mm in width. Number — Typically 2 per leaf bud and up to 6 per shoot tip. Length — Approximately 6 to 10 millimeters. Form — Lanceolate in form with a serrated margin. Color — Green (RHS Yellow Green Group 145 A) when young but changing to a yellow-brown (RHS Greyed-Orange Group 176 B) color with advancing senescence. The stipules are considered to be early deciduous.

Flowers:

*Flower buds.*—Generally — The floral buds are considered to be medium in size, (16.0 mm long and 9.0 mm wide), plump to slightly pointed in form, and moderately free relative to the bearing shoot.

*Flower buds.*—Color — The bud scales are gray-brown, (approximately RHS Greyed Orange Group 165 B). The buds are considered hardy under typical central San Joaquin Valley climatic conditions.

*Hardiness.*—No winter injury has been noted during the several years of evaluation in the Central San Joaquin Valley. The current variety has not been intentionally subjected to drought or heat stress and therefore this information is not available.

*Blooming type.*—Considered average to slightly larger than average in relation to other nectarine cultivars commonly growing in the Central San Joaquim Valley. Date of bud burst was observed on Feb. 28, 1998 and lasted approximately 9 days. Date of full bloom was observed on Mar. 3, 1998.

*Flower type.*—The variety is considered to be a showy type flower.

*Flower diameter.*—Flower diameter at full bloom is approximately 39 to 47 millimeters.

*Bloom quantity.*—Considered abundant.

*Flower bud frequency.*—Normally 1 to 2 buds appear per node, although 1 bud per node is more common.

*Petal size.*—Generally — Considered medium-large for the species. Length — Approximately 17 to 22 millimeters. Width — Approximately 17 to 21 millimeters.

*Petal shape.*—Broadly ovate.

*Petal count.*—Nearly always 5.

*Petal texture.*—Glabrous.

*Petal color.*—Light pink when young (approximately RHS Red Purple Group 65 C), and with advancing senescence it displays a medium pink (RHS Red Purple Group 65 D). The lower portion of the flower petal is typically darker than the apical portions and exhibits medium dark pink coloration (RHS Red-Purple 66D).

*Fragrance.*—Slight to absent.

*Petal claw.*—Form — The claw is considered truncate in shape and has a medium size when compared to other similar varieties. Length — Approximately 2 to 3 millimeters. Width — Approximately 1 millimeter.

*Petal margins.*—Generally — Edge of the margin surface is smooth, but the plane of the margin is considered variable, to moderately undulate.

*Petal apex.*—Generally — The petal apices appear slightly domed.

*Flower pedicel.*—Length — Considered medium-short, and having an average length of approximately 2.0 to 3.0 millimeters. Diameter — Considered average, approximately 2 millimeters. Color — Bright green (RHS Yellow Green Group 144 D).

*Floral nectaries.*—Color — Dull orange, to an orange-gold color (approximately RHS Orange Red Group 31 A). The color of the nectaries become more dull and slightly darker with advancing senescence.

*Calyx.*—Surface Texture — Generally glabrous and displaying a slight ribbing. Color — A dull red, (approximately RHS Greyed-Purple Group 184 A).

*Sepals.*—Surface Texture — The surface has a medium length, wooly, and gray (RHS Greyed Purple Group 183 A) colored pubescence. Number — Generally 5 per flower. Size — Average, and ovate in form. Typically 5.0 mm wide and 8.0 mm long. Color — A dull red, (approximately RHS Greyed Purple Group 178 A).

*Anthers.*—Generally — Average in size. Color — Red to reddish-orange dorsally, (approximately RHS Greyed Purple Group 187 D). Pollen Production — Pollen is abundant, and has a yellow-gold color, (approximately RHS Orange 26 A).

*Filaments.*—Size — Variable in length, approximately 12 to 14 millimeters. Color — Pink, (RHS Red Purple Group 66 D), and darkening with advanced maturity.

*Pistil.*—Generally — Average in size. Length — Approximately 13 to 16 millimeters, including the ovary. Color — Considered a very pale green, at mid-bloom, (approximately RHS Yellow Green Group 154 D), and becoming slightly more yellowish (RHS Yellow Green Group 145) with advancing senescence. Surface Texture — Glabrous.

Fruit:

*Maturity when described.*—The present variety of fruit is described, as it would be found in its firm ripe condition at full commercial maturity. In this regard, the fruit of the present variety was first picked on approximately May 25, 1998. The date of last pick of the same fruit in 1998 was approximately Jun. 5, 1998 under the ecological conditions prevailing in the San Joaquin Valley of Central California.

*Size.*—Generally — Medium in size, and considered moderately uniform. Average Cheek Diameter — Approximately 74 to 77 millimeters. Average Suture Diameter — Approximately 75 to 79 millimeters. Average Axial Diameter — Approximately 74 to 77 millimeters.

*Fruit weight.*—Not available. This is highly dependent on cultural practices, and therefore is not distinctive of this present variety.

*Fruit form.*—Generally — Globose in its lateral aspect. The fruit is generally uniform in symmetry with a rounded form when viewed from the apical aspect.

*Fruit suture.*—Generally — The fruit suture appears as a thin line, which extends from the base to the apex, and which appears slightly deeper, basally, within the stem well, and apically on both sides of the pistil point. No readily apparent callousing or stitching exists along the suture line.

*Suture.*—Color — The suture normally is the same color as the underlying blush, both where the orange-yellow background color, (RHS Orange Group 24 C) and the red orange color, (RHS Red Group 46 A to 46 B) occur.

*Ventral surface.*—Form — Considered uniform.

*Stem cavity.*—Size — Considered moderately shaped for the species.

*Width.*—Approximately 18–20 millimeters.

*Length.*—Approximately 27–30 millimeters.

*Depth.*—Approximately 8 to 10 millimeters.

*Form.*—Considered narrowly oval.

*Fruit base.*—Generally — Considered truncate in form, and uniform.

*Fruit apex.*—Generally — Considered depressed and usually recessed below the height of the apical shoulders.

*Fruit stem.*—Generally — Considered medium in length, approximately 8 to 9 millimeters.

*Diameter.*—Approximately 3 to 4 millimeters.

*Color.*—Generally a pale yellow-green, (approximately RHS Yellow Green Group 145 B).

*Fruit skin.*—Generally — Considered average in thickness. Surface Texture — The variety has a glabrous surface. Skin Acidity — Considered substantially neutral.

*Tenacious to flesh.*—Yes at commercial maturity.

*Tendency to crack.*—Not observed.

*Skin color.*—Generally — Variable, with approximately 80% to 90% of the fruit surface covered with a brilliant crimson red blush.

*Blush color.*—The blush color is generally more prevalent apically. This red blush color ranges from a dark red, (RHS Red Group 46 A and B) to an orange red, (RHS Orange Red Group 33 B), with many degrees of shading and blending occurring between these extremes.

*Skin ground color.*—This is generally present in variable percentages covering approximately 10% to 20% of the fruit's surface. The skin ground color is a yellow-golden, (RHS Yellow Orange Group 22 A to 24 C).

*Flesh color.*—Generally — Considered variable, from a yellow-orange color, (RHS Yellow Orange Group 21 C to 21 A).

*Flesh fibers.*—Generally — Present, numerous, fine and light colored. These fibers are present throughout the flesh.

*Stone cavity.*—Red, (approximately RHS Red Group 45 B) to a yellow orange, (approximately RHS Yellow Orange Group 18 B).

*Flesh texture.*—Generally — The flesh is considered firm and fine at full commercial maturity. The flesh texture is considered non-melting.

*Ripening.*—Generally — The fruit of the present variety ripens evening.

*Flavor.*—Considered very sweet and having moderate acidity. The flavor is considered both pleasant and balanced.

*Aroma.*—Pleasant and abundant.

*Eating quality.*—Generally — Considered very good to excellent and well above average when compared to other common varieties which ripen in the same season.

Stone:

*Attachment.*—Generally — The stone is considered a true freestone at full commercial maturity.

*Stone size.*—Generally — Considered medium small for the species.

*Length.*—Approximately 24 to 28 millimeters.

*Width.*—Approximately 22 to 23 millimeters.

*Thickness.*—Approximately 17 to 19 millimeters.

*Fibers.*—Generally — A few medium length fibers are attached alone the entire surface of the stone.

*Stone form.*—Generally — The stone is considered oval.

*Stone base.*—The stone is generally considered truncate.

*Base angle.*—The base angle of the stone is variable, but most frequently is considered truncate to slightly oblique to the stone axis.

*Hilum.*—Generally — Considered medium in size, and relatively well defined. The hilum is approximately 5 to 7 millimeters long and approximately 3 to 4 millimeters wide. Form — Considered oval.

*Apex.*—Shape — The stone apex is raised and has an acute tip.

*Stone shape.*—Considered variable. The stone is normally unequal, although occasionally it may appear nearly equal.

*Stone surface.*—Surface Texture — Generally, considered medium in roughness and exhibits substantial pitting laterally. Substantial grooving is apparent over the apical shoulders. Surface pitting is prominent, generally, and is more frequently present basally. Ridges — Numerous fine ridgs are present basally and converge towards the base of the stone.

*Ventral edge.*—Width — Considered average, and having a dimension of approximately 5 to 7 millimeters at mid-suture. The wings are most prominent over the basal area.

*Dorsal edge.*—Considered full, heavily grooved, and having jagged edges. The dorsal edge is moderately eroded over the apical shoulder.

*Stone color.*—The color of the dry stone is approximately a light to medium brown, (RHS Orange Red Group 34 C).

*Tendency to split.*—No splitting noted.

*Kernel.*—Generally — gelatinous and inmature at the time of ripening.

*Use.*—The subject nectarine variety 'Burnectone' produces fruit which are ripe for harvesting in the early season. Further, the fruit is considered very firm, has a highly attractive exterior color, and is useful for both local and long distance shipping.

*Keeping quality.*—Fruit has stored well up to 15 days after harvest at temperatures of about 1° C.

*Resistance to insects and disease.*—No particular susceptibilities were noted.

*Shipping quality.*—Well above average.

Although this new variety of nectarine tree possesses the described characteristics noted above, as a result of the growing conditions prevailing in the central part of the San Joaquin Valley of central California, it is to be understood that variations of the usual magnitude and characteristics incident to changes in growing conditions, fertilization and pruning and pest control are to be expected.

Having thus described and illustrated our new variety of nectarine tree, what we claim as new and desire to secure by Plant Letters Patent is:

1. A new and distinct variety of nectarine tree substantially as illustrated and described, and which has been denominated varietally as 'Burnectone', and which is characterized as to novelty by producing a freestone nectarine which is ripe for commercial harvesting and shipment under the ecological conditions prevailing in the central San Joaquin Valley of California from May 25 to June 5.

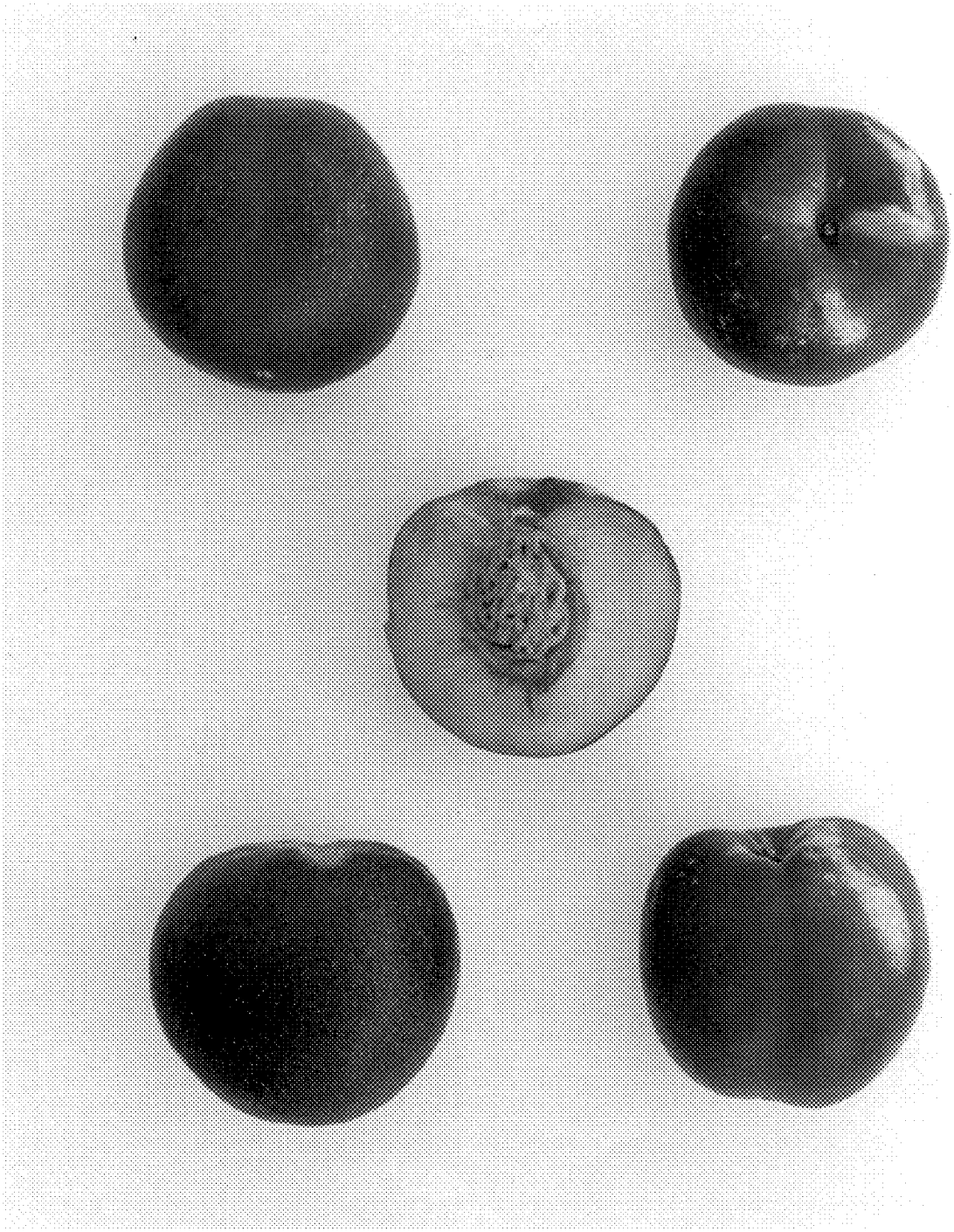

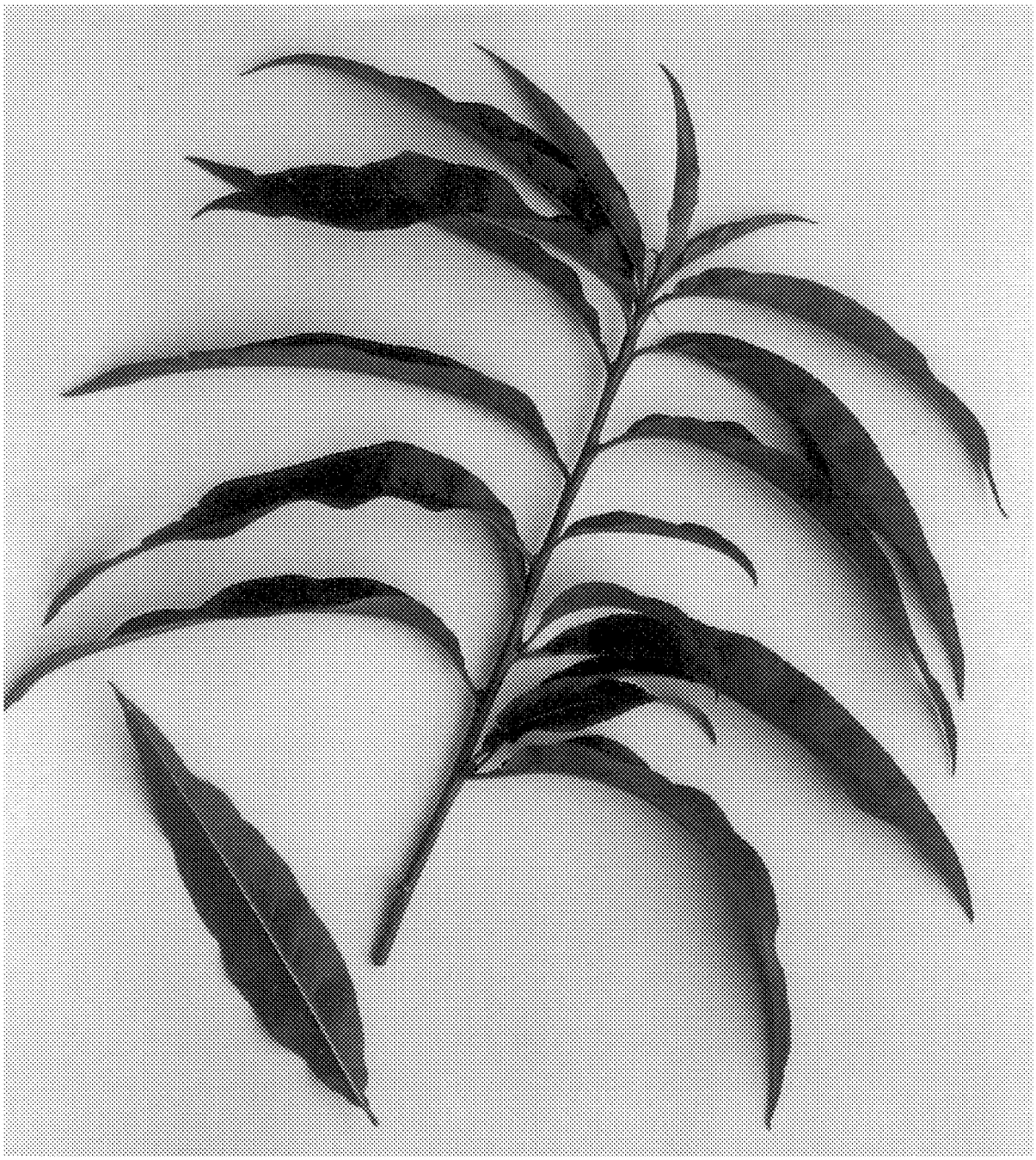

* * * * *